(12) United States Patent
Lehmann et al.

(10) Patent No.: US 6,440,932 B1
(45) Date of Patent: Aug. 27, 2002

(54) PHARMACEUTICAL COMBINATION PREPARATIONS CONTAINING ERYTHROPOIETIN AND MODIFIED HAEMOGLOBINS

(75) Inventors: Paul Lehmann, Worms; Jürgen Feuerstein, Ladenburg; Michael Harold Town, Oberhausen, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/446,378

(22) PCT Filed: Jun. 3, 1998

(86) PCT No.: PCT/EP98/03299

§ 371 (c)(1),
(2), (4) Date: Feb. 7, 2000

(87) PCT Pub. No.: WO98/58660

PCT Pub. Date: Dec. 30, 1998

(30) Foreign Application Priority Data

Jun. 21, 1997 (EP) .............................. 97110168

(51) Int. Cl.⁷ .................. A61K 38/16; A61K 38/00; A01N 37/18; A01N 38/00
(52) U.S. Cl. ................. 514/8; 514/2; 514/21
(58) Field of Search .................. 514/8, 2, 21

(56) References Cited

U.S. PATENT DOCUMENTS 5,541,158 A * 7/1996 Vance et al. .................. 514/8

FOREIGN PATENT DOCUMENTS

| EP | 0205564 | 12/1986 |
|---|---|---|
| EP | 0411678 | 2/1991 |
| EP | 19535571 A | 3/1997 |
| WO | WO 9524213 | 9/1995 |
| WO | WO 96/15805 | 5/1996 |
| WO | WO 9808537 | 3/1998 |

OTHER PUBLICATIONS

Feola, M. et al., "Clinical Trail of a Hemoglobin Based Blood Substitute in Patients with Sickle Cell Anemia", Surgery, Gynecology and Obstetrics, vol. 174, pp. 379–386 (1992).*

* cited by examiner

Primary Examiner—Kenneth R. Horlick
Assistant Examiner—Teresa Strzelecka
(74) Attorney, Agent, or Firm—George W. Johnston; Patricia S. Rocha-Tramaloni

(57) ABSTRACT

The present invention provides a pharmaceutical combination preparation comprising an erythropoietin preparation that provides active erythropoietin and at least one modified haemoglobin wherein the erythropoietin preparation and modified haemoglobin can be present in separate forms of administration or in a single form of administration. The pharmaceutical combination preparations of the present invention can be used to treat manifest anemias with or without iron utilization disorders.

3 Claims, No Drawings

PHARMACEUTICAL COMBINATION PREPARATIONS CONTAINING ERYTHROPOIETIN AND MODIFIED HAEMOGLOBINS

BACKGROUND OF THE INVENTION

The invention is concerned with pharmaceutical combination preparations containing erythropoietin preparations and one or more modified haemoglobins. The combination preparations are especially useful for the treatment of manifest anaemias.

The object of the present invention is a pharmaceutical combination preparation which comprises a) individual administration forms of an erythropoietin preparation suitable for the individual dosing of the active substance in an amount of 3,000–7,000 U and b) 50–100 ml of one or more modified haemoglobins, with the erythropoietin preparation and modified haemoglobin being present in separate administration forms or in a single administration form.

The macromolecule ferritin (molecular weight at least 440 kD depending on the iron content) plays a significant role in the diagnosis of anaemias. An estimation of the fullness level of the iron reservoir is possible by determining the ferritin and the transferrin saturation (M.Wick, W. Pingerra, P. Lehmann "Ferritin in iron metabolism and diagnosis of anaemias", pages 5–22, 38–50, 65–77, 94–97, $2^{nd}$ expanded edition 1994, published by Springer Vienna, New York), with the totality of the iron stored as basic ferritin in the depot organs liver, spleen and bone marrow amounting to about 800–1200 mg. A lower ferritin concentration is the definitive characteristic for detecting iron deficiency states and their difference from other causes of hypochromic anaemia, such as e.g. chronic inflammations and tumours.

It is known to treat transfusion-mediated anaemias in haemodialysis patients with recombinant erythropoietin (rhEPO), with it being necessary as a rule to carry out an iron substitution in parallel to the EPO therapy. This iron substitution is effected by the intravenous administration of iron(III) salts, with two intravenously administerable iron preparations being available on the German medicament market at present. These are the medicaments "Ferrlecit" and "Ferrum Vites". "Ferrlecit" is an iron(III) gluconate complex, while "Ferrum Vites" is an iron(III) oxide saccharate complex.

It has, however, become evident that in the case of manifest anaemias with manifest iron deficiency and iron utilization disorders (<30 mg/dl ferritin) iron substitution with the mentioned preparations has disadvantages, since for the treatment of manifest anaemias relatively large amounts of a pharmacologically harmless iron salt have to be infused. The use of the aforementioned iron preparations holds the possibility of unexpected circulatory reactions up to collapse, especially when large amounts have to be injected relatively rapidly.

In WO 96/15805 there is described a haemoglobin therapy for haemodialysis according to which very low doses of stroma-free haemoglobin are administered over a period of 10 to 45 minutes in order to achieve a haemostabilization and to avoid a lowering of blood pressure in sensitive patients. However, this described therapy is not successful in the case of manifest iron deficiency anaemias.

Also, WO 95/24213 describes the use of natural or recombinant haemoglobin or their chemically modified derivatives for anaemia treatment. Furthermore, this document discloses the combined administration of one of the aforementioned haemoglobins with one or more haematopoietic growth factors, inter alia with EPO. Examples 4 and 5 as well as some of the Figures show that a combined administration of EPO and rh haemoglobin lead to an increased haematopoesis.

However, this document does not disclose a practical therapeutic regime for an optimal regulation and treatment of patients with manifest anaemias. Also, it is not evident therefrom, as in the case of patients treated with EPO, that it is possible to produce an optimal EPO effect without avoiding an EPO resistance.

SUMMARY OF THE INVENTION

It has now been found that the use of relatively high infusion amounts of 50–100 ml of haemoglobin (about 100–200 mg $Fe^{2+}$) together with 3,000–7,000 U of EPO is surprisingly advantageous for the treatment of manifest anaemias (the abbreviation "IU" can also be used in place of the abbreviation "U" for International Units).

The object of the invention are accordingly also combination preparations which contain 3,000–7,000 U of EPO and 50–100 ml of one or more modified haemoglobins, with the EPO and the modified haemoglobin being present in separate administration forms or in a single administration form.

DETAILED DESCRIPTION OF THE INVENTION

In accordance with the invention 3,000–7,000 U of an erythropoietin preparation and 50–100 ml of one or more modified haemoglobins are used as the optimal dose depending on the clinical picture of the anaemia. Thus, in the case of manifest anaemias without iron distribution disorders, a high dose of $Fe^{2+}$, about 80–100 ml (about 160–200 mg $Fe^{2+}$), preferably 85–95 ml, in the form of a modified haemoglobin and a lower dose of EPO between 3,000 and 5,000 U is administered in accordance with the invention.

When there are iron distribution disorders in the case of manifest anaemias, a higher EPO dose of about 5,000–7,000 U of EPO, preferably 6,000–7,000 U, especially about 7,000 U of EPO, and a high $Fe^{2+}$ dose, about 80–100 ml, preferably about 100 ml, in the form of one or more modified haemoglobins is preferably administered.

For the treatment of iron utilization disorders in the case of manifest anaemias the combination preparation in accordance with the invention preferably contains 3,000–7,000 U of EPO and 80–100 ml of a modified haemoglobin, preferably about 5,000 U of EPO, and about 100 ml of one or more modified haemoglobins. For the treatment of manifest iron deficiency anaemias the combination preparation likewise preferably contains 3,000–7,000 U of EPO and 80–100 ml of a modified haemoglobin.

As modified haemoglobins in the meaning of the invention there are suitable in principle all haemoglobins described in WO 95/24213 page 20, line 15 to page 27, line 2. In particular, these are also cross-linked haemoglobins or cross-linked haemoglobin polymerizates, such as e.g. diacetylsalicylic acid (diaspirin), cross-linked haemoglobin (DCL-Hb) or other blood substitutes based on modified haemoglobins. For example, the following preparations come into consideration as modified haemoglobins: Hem Assist® (Baxter; DCL human Hb); PolyHeme® (Northfield, Upjohn, human Hb, cross-linked and polymerized); Hemopure® (Biopure, Upjohn; bovine Hb, polymerized); Optro® (Somatogen, Eli Lilly; recombinant human Hb); HemOlink® (Hemosol, Fresenius; human Hb, cross-linked and polymerized); PEG-modified bovine Hb (manufactured by Enzon; polyethylene glycol-modified Hb); polyoxyethylene-modified human Hb (manufactures Apex and Ajinimoto). The haemoglobins can also be used in accordance with the invention in the form of haemoglobin preparations which contain pharmaceutically compatible adjuvants known per se. Such preparations are described, for example, in WO 95/24213.

As suitable erythropoietin preparations in the meaning of the present invention there come into consideration those active substances which are comparable with respect to the physiological effect of human EPOs. Suitable EPO preparations are, for example, recombinant human EPO (rhEPO; see European Patent EP 0,205,564 or EP 0,411,678) or also corresponding modifications of these proteins. As modifications there come into consideration, for example, such proteins with molecular weights higher or lower than 34,000 Da (molecular weight of urinary EPO), likewise isoforms of the enzyme or proteins with different glycosylation. In particular, proteins chemically modified by PEG (polyethylene glycol) can also be used. Further, there basically also come into consideration such proteins which are derived by deletions, substitutions or additions from the amino acid sequence of the natural EPO with a length of 166 amino acids. These proteins have essentially comparable physiological properties to rhEPO. In particular, these proteins have biological properties which cause bone marrow cells to increase the production of reticulocytes and red blood corpuscles and/or to increase haemoglobin synthesis or iron uptake. In place of these proteins there can also be used low molecular substances, which are denoted as EPO mimetics, and which bind to the same biological receptor. These mimetics can preferably also be administered orally. The amount of such proteins or mimetics to be administered is determined by comparing the biological activity between EPO and these active substances.

The concentrations in accordance with the invention of EPO and haemoglobin-$Fe^{2+}$ permit in their combination an optimal anaemia treatment, especially the treatment of manifest anaemias. The treatment with the combination preparation is preferably effected once weekly, whereby the amount of haemoglobin of 300 ml per week should not be exceeded (e.g. 3×100 ml infusions).

In the meaning of the present invention there should be understood under the term "combination preparation" not only those medicament packs in which the EPO preparation and the haemoglobin are presented in juxtaposition in a finished marketable unit pack (so-called combination pack), but also those medicament packs which either contain a suitable amount of an EPO preparation or a suitable amount of a haemoglobin in the form of the respective individual preparations, with the individual preparations with respect to the amount of contents being presented such that they can be administered in the meaning of the invention for the combined dose with the respective other preparation. In these cases there is usually enclosed with the preparations from the pharmaceutical manufacturer or the medicament importer a medicament package insert which is required by law in many countries and in which are contained directions or information concerning the combined dose of the individual preparations.

The combination preparations can preferably be present in a single administration form in which the respective amounts of the EPO preparation and the haemoglobin are present in juxtaposition in one container.

This can be e.g. an injection solution or infusion solution or its lyophilizate, which, for example, is filled into ampoules. This administration form has the advantage that the EPO is stabilized by the modified haemoglobin during the production and storage of the administration form. In the case of a lyophilizate, the EPO, after its dissolution, is activated by the modified haemoglobin. The fixed combination of the two active substances in the form of a lyophilizate has the further advantage that it can be handled simply and safely. The lyophilizate is dissolved in the ampoule by the addition of pharmaceutically usual injection media and is administered intravenously.

It is also possible to administer the EPO preparation and the modified haemoglobin in the form of separate pharmaceutical formulations (free combination) simultaneously or, however, also in succession. This free combination, which can be made available in a unit pack, has the advantage of greater flexibility. Thus, these administration forms also enable the modified haemoglobins to be administered 1–3 days prior to the EPO administration.

This free combination, which can be made available in a single unit pack (medicament pack) also has the advantage that each patient to be treated can be prescribed a particular individual amount of an EPO preparation and of a haemoglobin. Furthermore, these combination preparations offer the advantage of greater safety when performing the therapy, since in each case the optimal synchronized amount of the individual preparation is fixed. A safe therapy and simple handling by the personnel performing the treatment or in the area of self medication performed by patients is guaranteed by the combination preparation in accordance with the invention.

Where the EPO preparation is made available as a lyophilizate, the medicament packs (combination packs) contain the corresponding amount of the EPO preparation in glass ampoules or in cartridges. The haemoglobin can be present in solid form (lyophilizate) or also in liquid form in a separate container. Further, the combination pack preferably contains a reconstitution solution in order to dissolve either the EPO lyophilizate alone or also together with the haemoglobin. If the haemoglobin is present as a ready-for-use solution, the solution can be mixed together with the EPO solution when the combined administration of EPO and haemoglobin has to be effected. Basically, the haemoglobin can also be made available as a concentrate for addition to conventional infusion solutions, by which means a longer administration over several hours can be effected.

Combination preparations in the meaning of the present invention are also those unit packs which in each case make available individual administration forms of the erythropoietin preparation or of the haemoglobin as independent medicaments, with the individual preparations being provided such that they contain the requisite amounts of the individual substances for the combination in accordance with the invention of the EPO preparation and the hemoglobin. As a rule, the medicament packs contain the previously described package insert containing corresponding instructions for the combined administration with EPO or with haemoglobin in the required amount. A corresponding instruction can also be present as a pack imprint on the medicament pack (secondary packaging) or on the primary packaging (ampoule, blister strips, etc.). Thus, in the case of the EPO-containing medicament with 3,000–7,000 U of EPO it is, for example, indicated thereon that this preparation should especially be administered together with a haemoglobin preparation containing 50–100 ml of one or more modified haemoglobins. In the case of the haemoglobin preparation there is a reverse indication to the combined administration with 3,000–7,000 U of an erythropoietin preparation.

A further possibility for providing the EPO preparation comprises making available corresponding multi-dose preparations which contain the EPO preparation in higher amounts compared with individual doses. These preparations are especially suitable for use in clinics in which a large number of patients are treated daily. These multi-dose preparations contain the EPO preparation in dosages of up to 500,000 U, especially up to 100,000 or 50,000 U. The multi-dose preparations have the advantage that they permit the skilled medical personnel to withdraw any dosage of the EPO preparation, for example by withdrawing corresponding amounts by volume of the finished injection solution. This is especially advantageous in the treatment of patients with different dosage requirements of the active substance or in the treatment of children in which a lower dosage of the EPO preparation is required. From an injection solution of, for example, 100,000 U of EPO, preferably freshly prepared at the beginning of the day, there can be performed, circumstances permitting, all patient treatments required during this day without the need to prepare separate injection solutions for each of the individual patients. This can lead to a significant time saving or to an easing of the burden of work for skilled medical personnel. Preferably, the individual EPO dosages are withdrawn in the range of 3,000 U, 5,000 U and 7,000 U.

The multi-dose preparations can also be present in the form of solutions, which are filled into cartridges. These cartridges are suitable for use in so-called pens, which permit administration by patients themselves and an individual dosage withdrawal. For example, these cartridges contain the EPO preparation in an amount of 10,000 or 20,000 U, whereby different dosing intervals can be realized by appropriate adjustment of the withdrawal volume.

The production of the pharmaceutical administration forms of the invention is effected according usual processes known in galenical technology with pharmaceutically usual adjuvants. The process for the production of the pharmaceutical combination preparation in accordance with the invention and the pharmaceutical unit pack, which contains the combination of preparations in accordance with the invention, are likewise objects of the invention.

In carrying out the therapy, the diagnostic parameters ferritin and transferrin saturation have to be controlled. The ferritin value is in the normal range when it amounts to 400 $\mu$g/l±50%. The transferrin saturation should amount to 20–40%.

The invention will be illustrated hereinafter in more detail on the basis of working Examples.

EXAMPLE 1

Patients with manifest iron deficiency (ferritin <12 ng/ml, transferrin saturation <15% and haemoglobin <12 g/dl) are given by infusion 5,000 U of rhEPO once per week and 100 ml of a modified haemoglobin preparation, preferably DCL-Hb, three times per week. This treatment is repeated for a further five weeks until the values for ferritin, transferrin saturation and haemoglobin or haemocrit lie in the normal range.

What is claimed is:

1. A method of treating manifest anemias in a patient comprising administering to the patient once weekly a pharmaceutical combination preparation containing an erythropoietin preparation that provides active erythropoietin in an amount of from about 3000 U to about 7000 U, and from about 50 ml to about 100 ml of at least one modified hemoglobin so as to correspond to from about 100 mg to about 200 mg of $Fe^{2+}$.

2. The method of claim 1 wherein the manifest anemias include iron utilization disorders, the method comprising administering to a patient once weekly a pharmaceutical combination preparation containing an erythropoietin preparation that provides active erythropoietin in an amount of from about 3000 U to about 7000 U, and from about 50 ml to about 100 ml of at least one modified hemoglobin so as to correspond to from about 100 mg to about 200 mg of $Fe^{2+}$.

3. The method of claim 1, wherein the manifest anemias do not include iron utilization disorders, the method comprising administering to a patient once weekly a pharmaceutical combination preparation containing an erythropoietin preparation that provides active erythropoietin in an amount of from about 3000 U to about 5000 U, and from about 85 ml to about 95 ml of at least one modified hemoglobin so as to correspond to from about 170 mg to about 190 mg of $Fe^{2+}$.

* * * * *